United States Patent [19]

Hoover

[11] Patent Number: 4,855,303

[45] Date of Patent: Aug. 8, 1989

[54] FLUORINE CONTAINING RENIN INHIBITORS

[75] Inventor: Dennis J. Hoover, Ledyard, Conn.

[73] Assignee: Pfizer Inc., New York, N.Y.

[21] Appl. No.: 206,079

[22] Filed: Jun. 10, 1988

Related U.S. Application Data

[63] Continuation-in-part of Ser. No. 68,989, Jul. 1, 1987.

[51] Int. Cl.$^4$ .......... A61K 37/43; C07K 5/05
[52] U.S. Cl. ........................ 514/18; 530/331
[58] Field of Search ........................ 530/331; 514/18

[56] References Cited

FOREIGN PATENT DOCUMENTS 0220665 5/1987 European Pat. Off. .
2171103 8/1920 United Kingdom .

Primary Examiner—Delbert R. Phillips
Attorney, Agent, or Firm—Peter C. Richardson; J. Trevor Lumb; James M. McManus

[57] ABSTRACT

Polypeptides containing fluorinated cyclostatine derivatives as antihypertensive agents.

13 Claims, No Drawings

FLUORINE CONTAINING RENIN INHIBITORS

CROSS REFERENCE TO RELATED APPLICATION

This application is a continuation-in-part of copending application Ser. No. 068,989, filed July 1, 1987.

BACKGROUND OF THE INVENTION

The proteolytic enzyme renin, which has a molecular weight of about 40,000, is produced in and secreted into the blood by the kidney. It is known to be active vivo in cleaving the naturally-occurring plasma glycoprotein angiotensinogen, in the case of human angiotensinogen at the bond between the leucine (10th) and valine (11th) amino acid residues at the N-terminal end of the angiotensinogen:

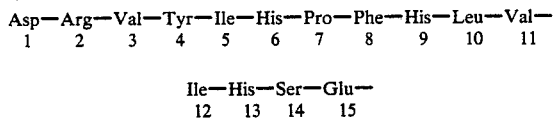

The circulating N-terminal decapeptide (angiotensin I) formed by the above cleaving action of renin is subsequently broken down by the body to an octapeptide known as angiotensin II. Angiotensin II is known to be a potent pressor substance, i.e., a substance that is capable of inducing a significant increase in blood pressure, and is believed to act by causing the constriction of blood vessels and the release of the sodium-retaining hormone aldosterone from the adrenal gland. Thus, the renin-angiotensinogen system has been implicated as a causative factor in certain forms of hypertension and congestive heart failure.

One means of alleviating the adverse effects of the functioning of the renin-angiotensinogen system is the administration of a substance capable of inhibiting the angiotensinogen-cleaving action of renin. A number of such substances are known, including antirenin antibodies, pepstatin and naturally-occurring phospholipid compounds. European Patent Application No. 45,665 (published Feb. 12, 1982) discloses a series of renin-inhibiting polypeptide derivatives of the formula

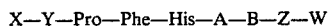

in which X may be hydrogen or an amino-protecting group, Y may be absent, B is a lipophilic amino acid residue, Z is an aromatic amino acid residue, W may be hydroxyl and A may be, inter alia,

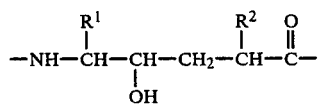

with each of $R^1$ and $R^2$ being a lipophilic or aromatic side chain. According to the definitions set forth in this published patent application, it is not contemplated that either A or Z could be statine or that B could be lysine.

European Patent Application No. 77,028A (published Apr. 20, 1983) discloses a series of renin-inhibiting polypeptide compounds having a non-terminal statine or statine derivative residue. Included within this series are compounds having a phenylalanine-histidine-statine sequence.

European Patent Application No. 132,304A also discloses the use of statine containing polypeptides as renin-inhibiting antihypertensive agents, and European Patent Application No. 114,993A discloses polypeptides containing cyclostatine, useful as renin-inhibiting antihypertensive agents.

Certain polypeptides containing fluoroketones related to statine are reported to be inhibitors of pepsin (Gelb, et al., *Biochemistry*, 24, 1814 (1985)).

PCT Application No. WO87/02675 claims a series of polypeptides containing 2,2-difluorocyclostatine.

SUMMARY OF THE INVENTION

It has now been found that certain fluorine containing polypeptides are useful as renin-inhibiting agents and have application in the treatment of hypertension and congestive heart failure.

This series of novel compounds consist of polypeptides of the formula

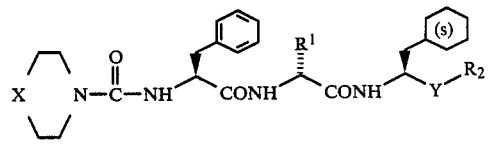

and a pharmaceutical acceptable salt thereof, wherein X is O or NH; $R_1$ is alkyl of one to six carbon atoms, imidazol-4-ylmethyl or methylthiomethyl; Y is

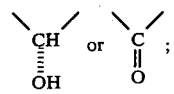

and $R_2$ is $CF_2CONHCH_3$, $CF_3$ or

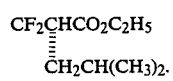

A preferred group of compounds are those wherein X is O and $R_1$ is alkyl of one to six carbon atoms. Especially preferred within this group of compounds is the compound where $R_1$ is n-butyl, Y is

and $R_2$ is $CF_2CONHCH_3$, where $R_1$ is n-butyl, Y is

and $R_2$ is $CF_2CONHCH_3$, where $R_1$ is n-butyl, Y is

and $R_2$ is $CF_3$, where $R_1$ is n-butyl, Y is

and $R_2$ is $CF_3$ and where $R_1$ is n-butyl, Y is C=O and $R_2$ is

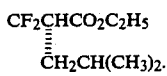

A second preferred group of compounds are those wherein X is NH and $R_1$ is alkyl of one to six carbon atoms. Especially preferred within this group of compounds is the compound where $R_1$ is n-butyl, Y is

and $R_2$ is $CF_2CONHCH_3$, where $R_1$ is n-butyl, Y is

and $R_2$ is $CF_2CONHCH_3$.

The present invention also includes a method for treating hyptertension in a mammal which comprised administering to said mammal an antihypertensive effective amount of the compounds of the present invention and a pharmaceutical composition comprised of the compounds of the present invention and a carrier.

The present invention is also meant to include renin inhibitors of the formula

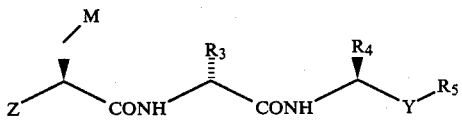

where Z is B—(C)$_m$—(A)$_p$ where B is $(C_1$-$C_4)$alkoxy, $(C_1$-$C_4)$alkylamino, di-$(C_1$-$C_4)$alkylamino, hydroxy(C-2-$C_4$)alkylamino, alkoxy($C_2$-$C_4$)alkylamino, $(C_1$-$C_4)$alkyl, morpholino, thiomorpholino, thiomorpholino sulfoxide, thiomorpholino sulfone, piperazino, 4-$(C_1$-$C_4)$alkanoylpiperazino, 4-$(C_1$-$C_4)$alkoxycarbonylpiperazino, 4-$(C_1$-$C_4)$alkylpiperazino, $(C_1$-$C_4)$alkoxy-COCH$_2$N(CH$_3$)— or N-proline($C_1$-$C_4$)alkyl ester; C is C=O; A is NH or O; and m and p are each 0 or 1;

M is phenyl, p-methoxyphenyl, benzyl or naphthyl;

$R_3$ is $(C_1$-$C_4)$alkyl, $(C_1$-$C_4)$alkylthioalkyl, $(C_2$-$C_4)$alkoxyalkyl, imidazol-4-ylmethyl;

$R_4$ is i-propyl, cyclohexyl or phenyl;

Y is C=O, C(H)—OR' or C(H) OR' where R' is hydrogen; and $R_5$ is $CF_2CONH(C_1$-$C_4)$alkyl, $CF_3$ or

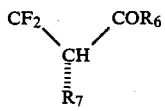

where $R_7$ is i-propyl or i-butyl and $R_6$ is alkoxy of one to six carbon atoms, $(C_1$-$C_4)$alkylamino or di$(C_1$-$C_4)$alkylamino; with the proviso that when m is 0, p is 0.

As previously indicated, the present invention embraces pharmaceutically acceptable salts of the biologically active compounds. Such salts are those which are non-toxic at the dosages administered. Since compounds of the invention may contain both basic and acidic groups, both acid addition and alkali addition salts are possible. Pharmaceutically acceptable acid addition salts include e.g., the hydrochloride, hydrobromide, hydroiodide, sulfate, bisulfate, phosphate, acid phosphate, acetate, lactate, maleate, mesylate, fumarate, citrate, acid citrate, tartrate, bitartrate, succinate, gluconate and saccharate salts. Pharmaceutically acceptable alkali addition salts include e.g., the sodium, potassium, calcium and magnesium salts. Conventional methods of forming acid addition and alkali addition salts may be employed.

In the interest of brevity, the commonly accepted abbreviated name of the individual aminoacids have been employed where possible. For example, the amino acid phenylalanine is abbreviated as Phe and histidine as His. The aminoprotecting group t-butoxycarbonyl is abbreviated as Boc and N-t-butoxycarbonyl on the imidazole of histidine as imBoc.

The modified cyclostatine containing fluorine in the structure is of the formula

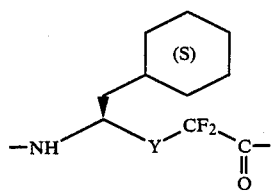

where Y is a previously defined, and are designated 2,2-difluoro-C-Sta. The corresponding ketones where Y is C=O are designated 2,2-difluoro-C-Statone.

All the natural amino acid contained in the structures of the instantly claimed compounds are of the L configuration, the naturally occurring configuration, unless otherwise noted.

DETAILED DESCRIPTION OF THE INVENTION

The compounds of this invention exhibit antihypertensive activity in vivo in mammals, including humans. At least a substantial portion of this activity results from their ability to inhibit the cleavage of angiotensinogen by renin. Although we do not wish to be limited by the following theory of mechanism, it is likely that the mechanism of the renin-inhibiting activity of the compounds of the invention is their selective binding (as compared to angiotensinogen) to renin. The compounds of the invention exhibit an enzyme-inhibiting activity that is selective for renin as against other beneficial enzymes such as cathepsin D. Because of their low molecular weights they exhibit favorable solubility characteristics in aqueous media, thus making oral administration feasible, and can be synthesized at a commercially realistic cost. The compounds of the present invention are also useful against congestive heart failure.

The compounds of the invention may be prepared by methods familiar to those skilled in the art. The basic sub-unit of the preferred chemical synthesis is the acylation of the unprotected alpha-amino group of an amino acid residue with an amino acid having an activated (for acylation purposes) carboxylic function and a suitable protecting group bonded to its own alpha-nitrogen to form a peptide bond between the two amino acid residues, followed by the removal of said protecting group. This synthesis sub-unit of coupling-deblocking is performed repeatedly to build up the polypeptide, starting from the C-terminal end of the molecular structure and working to the N-terminal end as described herein. The amino acid utilized to synthesize the compounds of the present invention are commercially available (as free acids, salts or esters, etc.) in both alpha-amino protected and alpha-amino unprotected forms.

Synthesis of the intermediate forming the skeleton of 2,2-difluorocyclohexylstatine is described in PCT International Publication No. WO87/02675.

The amides or esters, when subjected to hydrogen chloride in dioxane, lose the t-butoxycarbonyl protecting group from the amino moiety. Acylation of the resulting amino esters or amides are carried out using 1-hydroxybenzotriazole and a carbodiimide. Removal of the blocking group on imidazole with acetic acid-water gives the final product.

The ketone containing polypeptides of the present invention are prepared by oxidation of the corresponding (R) to (S) hydroxy polypeptides using dimethylsulfoxide and oxalyl chloride.

The activity of the compounds of the present invention as inhibitors of the angiotensinogen-cleaving activity of renin may be determined by studying (1) their ability to inhibit the angiotensinogen-cleaving activity of renin in vitro and (2) their ability to antagonize the exogenous renin-induced pressor response in vivo.

The compounds of the present invention can be administered as antihypertensive agents by either the oral or parental routes of administration, with the former being preferred for reasons of patient convenience and comfort. In general, these antihypertensive compounds are normally administered orally in dosages ranging from about 0.5 mg to about 50 mg per kg of body weight per day and 0.1 mg to about 5 mg per kg of body weight per day when given parenterally; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

The novel compounds of the invention can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired of oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The following examples illustrate the invention but are not to be construed as limiting the same.

General. TLC was performed on EM Merck silica 254 TLC plates eluting with: System A, 18/2/1 chloroform/ethanol/acetic acid HPLC was performed isocratically on a Beckman gradient system using two model 100 pumps, solvent mixer, and fixed wavelength 214 nM detector at 1.5 ml/min in various compositions of acetonitrile:pH 2.1 0.1M $KH_2PO_4$-phosphoric acid buffer (ratios specified below) on a Zorbax 25 cm×4.6 mm C-8 column.

EXAMPLE 1

Morpholinocarbonyl-Phe-Nle-2,2-difluoro-C-Sta N-methylamide (X=O, $R_1$=n—$C_4H_9$, Y=CH'''''OH and $R_2$=$CF_2CONHCH_3$)

2,2-Difluoro-(R)-3-hydroxy-(S)-4-amino-5-cyclohexyl-N-methylvaleramide hydrochloride (2,2-difluoro-C-Sta N-methylamide hydrochloride), 252 mg, was dissolved in 2.5 ml dichloromethane, cooled in an ice bath and treated sequentially with triethylamine (151 ul, 1.3 equiv), 328 mg of morpholinocarbonyl-L-phenylalanyl-L-norleucine(Mor-Phe-Nle), 1-hydroxybenzotriazole hydrate (HBT, 193 mg, 1.0 equiv) and dicyclohexylcarbodiimide (DCC, 173 mg, 1.0 equiv) and the mixture was stirred overnight during which time the temperature rose to 15°–20° C. The mixture was filtered, the filtered solids were washed with dichloromethane and concentrated and the residue was dissolved in ethyl acetate. After being stirred for a few minutes, the suspension was filtered, and the filtrate was washed with 1N sodium hydroxide solution (2×ca. 5 ml), brine, dried over magnesium sulfate and concentrated giving colorless foam which was chromatographed on 30 g silica packed in 1% ethanol/methylene chloride (v/v), eluting with 700 ml each of 1%, 2% and 4% ethanol in methylene chloride. The title substance, 338 mg (63%), was obtained as a colorless powder, TLC Rf 0.53 in System A, HPLC in 50/50 MeCN/buffer, 6.97 min, 97% of UV integration to 12 minutes.

NMR (DMSO-d6), 250 mHz, partial, $\delta$, ppm: 0.88 (t, 3H, overlapping m, 1H), 1.0–1.85 (m, ca. 16H), 2.67 (m, 3H, NCH$_3$), 2.83 (dd, 1H), 3.0 (dd, 1H), 3.21 (m, 4H), 3.47 (m, 4H), 3.96 (dq, 1H), 4.17 (overlapping m, 2H) 4.33 (m, 1H), 6.0 (d, 1H), 6.68 (d, 1H), 7.13–7.5 (m, ca. 6H), 8.05 (d, 1H), 8.46 (m, 1H). FAB-MS (thioglycerol) m/e (rel. intensity): 201(11), 217(100), 218(11), 219(10), 233(16), 261(24), 265(22), 307(24), 325(11), 378(12), 638(76, MH+), 639(32).

EXAMPLE 2

Morpholinocarbonyl-Phe-Nle-epi-2,2-difluoro-C-Sta N-methylamide (X=O, R$_1$=n—C$_4$H$_9$, Y=CH⋯OH and R$_2$=CF$_2$CONHCH$_3$)

An approximately 1:1 mixture (270 mg) of 2,2-difluoro-(R)-3-hydroxy-(S)-4-amino-5-cyclohexyl-N-methylvaleramide and 2,2-difluoro-(S)-3-hydroxy-(S)-4-amino-5-cyclohexyl-N-methylvaleramide obtained from 2,2-difluoro-(R,S)-3-hydroxy-4-t-butoxycarbonylamino-5-cyclohexyl-valeramide ethyl ester was treated according to the procedure of Example 1 with triethylamine, Mor-Phe-Nle, HBT and DCC to give, after identical workup and chromatography, the title substance (266 mg, 47%) which was well separated from the slightly less polar isomer (product of Example 1 (160 mg, 28%).

TLC Rf 0.45 in TLC System 1, HPLC in 60/40 MeCN/buffer, 3.54 minutes, 94% of UV integration to 8 minutes. Under these conditions the product of Example 1 showed a retention time of 3.83 minutes. NMR (DMSO-d6, 250 mHz), partial, $\delta$, ppm.: 0.62 (m, 1H), 0.88 (t, 3H), 1.02–1.85 (m, ca. 16H), 2.67 (br, 3H, NCH$_3$), 2.83 (dd, 1H), 3.00 (dd, 1H), 3.21 (m, 4H), 3.48 (m, 4H), 3.94 (dq, 1H), 4.10 (m, 1H), 4.22 (m, 1H), 4.35 (m, 1H), 5.95 (d, 1H), 6.68 (d, 1H), 7.1–7.35 (m, ca. 6H), 7.69 (d, 1H), 7.97 (d, 1H), 8.58 (m, 1H). FAB-MS (thioglycerol) m/e (rel. intensity)=217(24), 233(48), 261(53), 265(33), 307(11), 378(27), 638(100, MH+), 639(39), 640(10).

EXAMPLE 3

Morpholinocarbonyl-Phe-Nle-2,2-difluoro-C-Statone N-methylamide (X=O, R$_1$=n—C$_4$H$_9$, Y=C=O and R$_2$=CF$_2$CONHCH$_3$)

A dry 15 ml flask capped with a septum and maintained under nitrogen was charged with 0.8 ml oxalyl chloride (1.2 equiv) and cooled to −65° C. Dimethylsulfoxide (48 ul, 2.2 equiv) was added followed after 3 minutes by a solution of 197 mg of the product of Example 2 (1.0 equiv) in 0.75 ml dichloromethane (the addition of this solution was accomplished by nitrogen pressure though a stainless steel cannula and took 3 minutes; another 0.25 ml dichloromethane was used to rinse in this material). The reaction temperature was raised to −30° C. for 45 minutes, then lowered to −60° C., whereupon 225 ul (5.0 equiv) of dry diisopropylethylamine was added. The cooling bath was replaced with an ice bath for 5 minutes and the reaction allowed to stir at ambient temperature for 5 minutes. Dichloromethane (ca 50 ml) was then added and the solution was washed with saturated aqueous sodium bicarbonate solution (3×2 ml), dried over magnesium sulfate, filtered and concentrated giving 230 mg of a colorless foam which was chromatographed on 18 g silica packed in 0.5% ethanol-dichloromethane, eluting with 500 ml each of 0.5%, 1%, 2% and 4% ethanol-dichloromethane. The title substance was obtained as a colorless powder (107 mg, 55%), along with 49 mg (25%) of unreacted starting material.

TLC Rf, System A, 0.60; HPLC in 50/50 MeCN-/buffer 5.92 minutes with a broad tail, 96% of total UV integration to 12 minutes. Under the same conditions the starting material (product of Example 2) gave a 5.15 peak. NMR (CDCl$_3$, 250 mHz), $\delta$, ppm. partial: 0.83 (t, 3H, overlapping 0.9 m), 1.0–1.9 (m, ca. 16H), 2.83 (d, 3H, NCH$_3$), 2.95 (dd, 1H), 3.05–3.35 (m, ca. 5H), 3.55 (m, 4H), 4.35, 4.50, 4.85 and 5.18 (m, 1H each), 7.03, 7.37, 7.45 (m, 1H, ea.), 7.1–7.3 (m, aromatic). FAB-MS [thioglycerol, m/e (rel. intensity)]: 233(82), 234(13), 259(12), 261(99), 262(18), 263(35), 374(18), 376(29), 636 (100, MH+), 637(37), 638(11).

EXAMPLE 4

N-(Morpholinocarbonyl-Phe-Nle)-(R)-2-hydroxy-(S)-3-amino-1,1,1-trifluoro-4-cyclohexylbutane (X=O, R$_1$=n—C$_4$H$_9$, Y=CH⋯OH and R$_2$=CF$_3$)

A. 2-nitroethylcyclohexane

An oven-dried 1 liter 3-necked flask fitted with dropping funnel, thermometer and 31 g sodium nitrite. The mixture was stirred at 5° C. while 50 g 2-cyclohexylethylbromide (Aldrich) was added over 5 minutes. The cooling bath was removed and the mixture was stirred at 25° C. for 18 hours, poured into 1.5 l cold water and the mixture was repeatedly extracted (4×150 ml) with petroleum ether which was washed with water (2×10 ml) and dried over magnesium sulfate. The solvent was removed at reduced pressure using a rotary evaporator and the residue was distilled through an 8" Vigreux column giving 18.3 g (41%) of the desired product boiling at 70°–80° C. and 2 mm Hg, preceded by 8 g of lower-boiling material gave 16.4 g, 40%, bp 62°–65° C. at 0.5 mm Hg of the title product.

B. 2-hydroxy-3-nitro-1,1,1-trifluoro-4-cyclohexylbutane

The product of Example 4A (1.52 g) was mixed with 200 mg potassium carbonate and 16.86 trifluoroacetaldehyde hydrate at 25° C., heated under nitrogen to 50° C. for 4 hours, refrigerated overnight for 14 hours, heated against at 60° C. for 8 hours and refrigerated overnight. The light yellow clear solution was chromatographed on 100 g silica in 1:10 ether-hexane giving 24 g of a light yellow oil which was rechromatographed on 300 g silica packed in 1:15 ether-hexane, eluting with 1 liter 1:15 and 2 liters 1:10 ether-hexane giving 20.2 g of a light yellow oil after solvent removal.

C. 2-hydroxy-3-amino-1,1,1-trifluoro-4-cyclohexylbutane

A 500 ml centrifuge bottle was charged with 20.1 g of the product of Example 4B, 250 ml absolute ethanol and 5 g of water-wet Aldrich Raney Nickel catalyst. The light blue solution was shaken under 45 p.s.i. hydrogen pressure for 20 hours, filtered through Celite which was washed with methanol and the filtrates were concentrated to give a waxy solid which was filtered and washed with 2×10 ml cold hexanes and dried to give 11.0 g of the title substance as a mixture of two racemic diastereomers. One gram of this material was chromatographed on 100 g silica packed in 1% ethanol/methylene chloride eluting with 500 ml each of 1%, 2%, 4%, 6% and 10% ethanol/methylene chloride. The less polar isomer (531 mg) was identified as the 2(R),3(S) isomer and the more polar isomer (433 mg) as the 2(S),3(S) isomer by their NMR spectra.

D. N-(morpholinocarbonyl-Phe-Nle)-(R)-2-hydroxy-(S)-3-amino-1,1,1-trifluoro-4-cyclohexylbutane This compound was prepared as a ca. 1:1 mixture with the corresponding 2(S),3(S) isomer. According to the general procedure for preparation and purification of the product of Example 1, 381 mg of the 2(R),3(S) isomer of Example 4C was coupled to 860 mg of Mor-Phe-Nle using 414 mg HBT and 453 mg DCC in 3 ml dichloromethane. The crude product was chromatographed on 40 g silica in 1:3, 1:2 and 1:1 ethyl acetate-hexane (1 l of each), giving 700 mg (69%) of the title substances as a colorless solid.

TLC Rf 0.35 in System A, HPLC in 60/40 MeCN-/buffer 7.47 minutes. NMR (CDCl$_3$, 300 mHz, δ, ppm. partial): 0.82 (t), 1.05–1.95 (m), 2.9–3.1 (m), 3.27 (m), 3.53 (m), 3.90, 4.17, 4.21, 4.70, 4.85, 5.27, 5.49, 5.83 (m), 6.04 (d), 7.1–7.3 (m), 7.4 (m), 7.54 (m), 8.02 (br). 19F NMR (CDCl$_3$), 300 mHz, δ, ppm from CFCl$_3$: Two doublets in 1:1 ratio- 101.07 (d, J=5.7 Hz), 100.83 (d, J=6.1 Hz), FAB-MS [thioglycerol, m/e (rel. intensity)]: 226(21), 233(91), 234(14), 259(17), 261(100), 262(17), 599(40, MH+), 600(16).

EXAMPLE 5

N-(Morpholinocarbonyl-Phe-Nle)-(S)-2-hydroxy-(S)-3-amino-1,1,1-trifluoro-4-cyclohexylbutane (X=O, R$_1$=n—C$_4$H$_9$, Y=CH—OH and R$_2$=CF$_3$)

The titled compound was prepared as a 1:1 mixture with the corresponding 2(R),3(R) isomer. According to the procedure used for the preparation of the product of Example 4D, 240 mg of the 2(S),3(S) isomer of Example 4C was coupled to Mor-Phe-Nle giving after analogous workup and purification 538 mg (85%) of the title substances as a colorless foam.

TLC Rf 0.38 in System A, HPLC in 60/40 MeCN-/buffer 8.26 minutes and 9.22 minutes, 1:1 ratio. 1H NMR (CDCl$_3$, 300 mHz, δ, ppm, partial): 0.89 and 0.91 (triplets), 1.05–2.0 (overlapping m), 2.85–3.05 (m), 3.05–3.35 (m), 3.58 (m), 3.96 (m), 4.22, 4.35 and 4.76 (m), 4.81 and 4.90 (d), 5.30 (m), 6.53, 6.67, 6.85 and 6.96 (d), 7.10–7.35 (m). FAB-MS [thioglycerol, m/e (rel. intensity)]: 217(20), 226(24), 233(67), 234(12), 259(13), 261(93), 262(93), 339(29), 583(22), 597(11), 599(100, MH+), 600(37).

EXAMPLE 6

N-(Morpholinocarbonyl-Phe-Nle)-3-(R,S)-amino-1,1,1-trifluoro-4-cyclohexylbutanone (X=O, R$_1$=n—C$_4$H$_9$, X=C=O and R$_2$=CF$_3$)

A solution of 200 mg of the product of Example 5 was added to a solution of 156 mg of the Dess-Martin periodinane (*J. Org. Chem.*, 1983, 45, p. 4155) and the suspension was stirred 20 minutes at 25° C. Ether (50 ml) was added, followed by 1.3N sodium hydroxide solution (20 ml), and stirring was continued 10 minutes. The layers were separated and the ether layer was washed with dilute sodium hydroxide solution, brine, dried over magnesium sulfate and concentrated giving 100 mg of a yellow solid which by NMR was 1:1 product/starting material. The solid was dissolved in 5 ml dichloromethane, treated sequentially with 45 ul trifluoroacetic acid and 1.0 equiv of the periodiane and the now homogeneous reaction mixture was stirred 0.5 hour at 25° C., diluted with ether, stirred with 1.3N sodium hydroxide solution for 10 minutes, separated, the organic layer washed with fresh sodium hydroxide solution, brine, dried over magnesium sulfate and concentrated to give 45 mg of a yellow solid. The aqueous layers were further extracted with dichloromethane (5×30 ml) which was dried and concentrated to give additional solid which combined with the first lot give 95 mg of the title substance as pale yellow flakes, TLC Rf 0.38 in System A, HPLC in 50/50 MeCN/buffer 5.43 and 5.72 minutes (35/64 ratio, respectively).

1H NMR (CDCl$_3$, 300 mHz, 67 , ppm, partial): 0.89 (t), 1.05–2.0 (m), 2.95 (dd, 1H), 3.1–3.35 (m), 3.60 (m, 4H), 4.32, 4.47, 4.80, 4.88 and 4.95 (m), 6.34 (d), 6.60 (m), 7.14–7.45(m). FAB-MS [thioglycerol, m/e (rel. intensity)]: 233(78), 234(12), 259(20), 261(100), 262(15), 597(50, MH+), 598(18).

EXAMPLE 7

Piperazinocarbonyl-Phe-Nle-2,2-difluoro-C-Sta N-methylamide (X=NH, R$_1$=nC$_4$H$_9$, Y=CH""OH R$_2$=CF$_2$CONHCH$_3$)

A. 1-t-butyloxycarbonyl-4-benzylpiperazine

A solution of 10.0 ml N-benzylpiperazine in 150 ml 2:1 dioxane-water was treated with aqueous sodium hydroxide solution to raise the pH to 12.0 and the 0° C. solution was treated with 18 ml di-t-butyldicarbonate. The pH was kept at 9.5–10.5 by addition of aqueous base. After 10 minutes 4 ml more di-t-butyl dicarbonate was added and after a few minutes the mixture was concentrated, extracted with ethyl acetate (5×), which was washed with brine and dried over magnesium sulfate. A clear oil (24.5 g) was obtained on solvent removal which was chromatographed on 350 g silica packed and loaded in 4% ethanol-1% triethylamine in dichloromethane (v/v/v). The column was eluted with 1 liter each of 4% EtOH/1% TEA and 6% EtOH/1% TEA. The fractions containing product were concentrated to give 18.9 g of a colorless solid which was rechromatographed on 600 g silica eluting with 1:4, 1:2 and 1:1 ethyl acetate/hexanes. The title substance, 14.2 g) TLC Rf 0.43 in 2:1 ethyl acetate/hexanes was obtained.

B. 1-t-butyloxycarbonylpiperazine

A solution of 7.70 g of the product of Example 7A in 75 ml methanol with 2.0 g 10% palladium-on-charcoal was shaken under 45 p.s.i. hydrogen pressure for 2.5 hours and filtered through Celite which was then washed with methanol. The filtrates were concentrated and the residue was coevaporated with ether and toluene giving an oily solid, 9.9 g. This was recrystallized from 75 ml boiling ether to give 6.92 g of colorless needles, TLC Rf 0.10.

C. N-t-butyloxycarbonylpiperazino-N'-carbonylphenylalanine benzyl ester

The product of Example 7B, 3.2 g, was dissolved in 30 ml dichloromethane and 3.65 g of (S)-2-isocyanato-3-phenylpropionic acid benzyl ester was added. After 15 minutes the concentrated mixture was chromatographed on 400 g silica in 30% ethyl acetate/hexanes eluting first with 6 liters 30% then 2 liters 40% ethyl acetate/hexanes giving after solvent removal 3.85 g of the title product as an oily solid, TLC Rf 0.24 in 1:1 ethyl acetate/hexanes.

D. N-t-butyloxycarbonylpiperazino-N'-carbonyl phenylalanine

A solution of 3.84 g of the product of Example 7C in 30 ml 10% acetic acid in methanol was shaken with 0.5 g 10% palladium-on-charcoal for 1.5 hours at 25° C. and 50 p.s.i. hydrogen pressure. The mixture filtered through Celite and concentrated gave after coevaporation with added toluene (2×) and ether (2×) 2.74 g of a colorless foam, TLC Rf 0.48 in System A.

E. N-t-butyloxycarbonylpiperazino-N'-carbonyl-Phe-Nle benzyl ester

According to the general procedure for preparation and purification of the product of Example 1, 1.00 g of norleucine benzyl ester hydrochloride, 8 ml dichloromethane, 700 ul triethylamine, 1.46 g of the product of Example 7D, 890 mg HBT, and 800 mg DCC gave after analogous isolation and purification 1.65 g of the title product as a colorless foam, TLC Rf 0.86 in System A.

F. N-t-butyloxycarbonylpiperazino-N'-carbonyl-Phe-Nle

According to the procedure for the preparation of the product of Example 7D, 1.64 g of the product of Example 7E gave 1.40 g of the title substance as a colorless foam, TLC Rf 0.54 in System A.

G. N-t-butyloxycarbonylpiperazino-N'-carbonyl-Phe-Nle-2,2-difluoro-C-Sta N-methylamide According to the procedure for the preparation and purification of the product of Example 1, 301 mg of 2,2-difluoro-C-Sta N-methylamide hydrochloride, 2.5 ml dichloromethane, 180 ul triethylamine, 491 mg of the product of Example 7F, 230 mg HBT and 206 mg DCC gave 573 mg of the title substance after analogous isolation and purification. TLC Rf 0.58 in System A, HPLC retention time 2.84 minutes in 80/20 acetonitrile-water.

H. piperazinocarbonyl-Phe-Nle-2,2-difluoro-C-Sta N-methylamide

The product (261 mg) of Example 7G was dissolved in 2.0 ml 4N hydrogen chloride-dioxane. After 45 minutes the suspension was concentrated, the residue coevaporated with added ether and dried giving 251 mg of the title substance as a colorless solid. HPLC 40/60 acetonitrile-buffer retention time 5.03 minutes. 1N NMR (250 mHz, DMSO-d6, δ, ppm, partial): 0.88 (t, 3H), 1.07–1.92 (overlapping m, ca. 16H total), 2.70 (d, 3H, NCH$_3$), 2.8–3.07 (m, ca. 6H total), 3.48 (m, 4H), 4.32 (m, 2H), 4.85 (m, 1H), 6.92 (d, 1H), 7.15–7.38 (m, ca. 6H), 8.11 (d, 1H), 8.43 (d, 1H), 9.07 (m, 2–3H). FAB-MS [thioglycerol, m/e (rel. intensity)] 217(16), 232(10), 260(44), 265(30), 378(10), 637(100, MH+), 638(40).

EXAMPLE 8

Piperazinocarbonyl-Phe-Nle-2,2-difluoro-C-Statone N-methylamide (X=NH, R$_1$=n—C$_4$H$_9$, Y=C=O and R$_2$=CF$_2$CONHCH$_3$)

A. N-t-butyloxycarbonyl-Phe-Nle-2,2-difluoro-C-Statone N-methylamide

A solution of 43 ul oxalyl chloride in 0.8 ml dichloromethane was cooled to −60° C. and treated with 64 ul dimethylsulfoxide in one portion. After 3 minutes a solution of 300 mg of the product of Example 7G in 0.8 ml dichloromethane was added (rinsing further with 0.25 ml dichloromethane). The solution was stirred at −30° C. for 45 minutes, cooled to −60° C. and treated over 30 seconds with 351 ul diisopropylethylamine, warmed to 0° C. for 5 minutes and brought to 25° C. for 5 minutes. The mixture was diluted with dichloromethane, washed with 3×2 ml saturated aqueous bicarbonate, brine, dried over sodium sulfate and concentrated giving 346 mg of a colorless foam which was chromatographed on 15 g silica in 3:1 ethyl acetate/hexanes, eluting with 500 ml of this solvent. A product (245 mg) was obtained by concentrating the appropriate fractions. TLC Rf 0.35 in ethyl acetate. Carbon-13 and fluorine-19 NMR showed resonance consistent with a single compound of greater than 90% purity.

B. piperazinocarbonyl-Phe-Nle-2,2-difluoro-C-Statone N-methylamide

The product of Example 8A (157 mg) was dissolved in 2.0 ml 4N hydrogen chloride-dioxane. After 40 minutes the mixture was concentrated, the residue coevaporated with ether and dried giving the title substance, 145 mg, as a colorless powder. TLC Rf 0.28 (the spotted plate was exposed to NH$_3$ vapor prior to elution in System A). HPLC in 40/60 MeCN/buffer showed a 5.73 minute peak with a broad tail. There was no contamination with the corresponding alcohol 7H (eluting at 5.03 minutes).

1H NMR (250 mHz, DMSO-d6, δ, ppm, partial): 0.88 (t, 3H), 1.02–1.88 (overlapping m, ca. 16H), 2.66 (d, 3H, NCH$_3$), 2.75–3.08 (overlapping m, ca. 6H), 3.48 (m), 3.97 (dd, 1H), 4.2 (m, 1H), 4.35 (m, 1H), 6.95 (d, 1H), 7.17–7.48 (m, 6–7H), 8.18 (d, 1H), 8.47 (d, 1H), 9.05 (br, 1H). FAB-MS [thioglycerol, m/e (rel. intensity)] 181(18), 201(20), 217(100), 219(11), 232(10), 260(47), 261(12), 289(20), 635(56, MH+), 636(20), 667(21), 743(14, MH++thioglycerol).

EXAMPLE 9

Morpholinocarbonyl-Phe-Nva-2,2-difluoro-C-Sta N-methylamide (X=O, R$_1$=n—C$_3$H$_7$, Y=CH OH and R$_2$=CF$_2$CONHCH$_3$)

A. butyloxycarbonyl-Norvaline-2,2-difluoro-C-Sta N-methylamide

According to the procedure for the preparation and purification of the product of Example 1, 143 mg of 2,2-difluoro-C-Sta N-methylamide hydrochloride, 1.0 ml dichloromethane, 86 ul triethylamine, 103 mg Boc-norvaline, 109 mg HBT and 98 mg DCC gave after analogous isolation and purification 162 mg of the title product, TLC Rf 0.68 in System A.

B. norvaline-2,2-difluoro-C-Sta N-methylamide

The product of Example 9A, 157 mg, was dissolved in hydrogen chloride-dioxane (1.5 ml). After 30 minutes the mixture was concentrated, the residue coevaporated with added ether and dried giving a colorless powder, 140 mg, TLC Rf 0.15 in System A.

C. morpholinocarbonyl-Phe-Nva-2,2-difluoro-C-Sta N-methylamide

According to the procedure for the preparation and purification of the product of Example 1, 130 mg of the product of Example 9B, 0.5 ml dichloromethane, 59 ul triethylamine, 90.4 mg of morpholinocarbonyl-Phe 75 mg of HBT and 67 mg of DCC gave 168 mg of the title substance as a colorless solid.

TLC Rf 0.54 in System A, HPLC retention time 2.48 minutes in 70/30 acetonitrile-buffer. 1H NMR (DMSO-d6, 250 mHz, δ, ppm, partial): 0.89 (t, 3H), 1.02–1.85 (m, ca. 16H), 2.67 (d, 3H, NCH$_3$), 2.73 (dd, 1H), 3.0 (dd, 1H), 3.21 (m, 4H), 3.48 (m, 4H), 3.97 (ddd, 1H), 4.23 (m, 2H), 4.34 (m, 1H), 6.0 (d, 1H), 6.67 (d, 1H), 7.13–7.35 (m, 5–6H), 7.4 (d, 1H), 8.05 (d, 1H), 8.45 (d, 1H). FAB-MS [thioglycerol, m/e (rel. intensity)] 233(85), 234(16), 261(100), 262(17), 265(89), 266(14), 364(38), 624(87, NH+), 625(31).

EXAMPLE 10

Ethyl (2S,5S)-2-isobutyl-3,3-difluoro-4-keto-5-N-(N-[morpholinocarbonyl-L-phenylalanyl]-L-norleucyl)-amino-6-cyclohexylhexanoate (X=O, R$_1$=n—C$_4$H$_9$, Y=C=O and

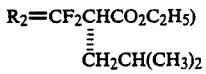

A. 1,1-difluoro-4-cyclohexyl-1-buten-3-ol 2,2-Difluorovinyllithium[1] was prepared by dropwise addition of sec-butyllithium in cyclohexane (88 mL of 1.4M, 0.123 mol, 1.0 equiv) during 10 minutes to a stirred solution of 1,1-difluoroethylene (15.3 g, 0.230 mol, 1.9 equiv) in THF (140 mL) and ether (20 mL). The reaction mixture was maintained between −100° and −93° C. during this addition and was subsequently stirred 10 minutes at −100° C. Cyclohexylacetaldehyde (15.6 g, 0.123 mol, 1.0 equiv) was added dropwise over 5 minutes (the reaction temperature rose to −89° C.), and the resulting mixture was stirred 1 hour between −110° and −93° C. Saturated aqueous NH$_4$Cl (50 mL) was then added, and the mixture was warmed to 0° C. and treated with ether (500 mL) and brine. After separation the organic layer was washed twice with 1N aqueous HCl, H$_2$O, aqueous saturated NaHCO$_3$, and dried over MgSO$_4$. Concentration at reduced pressure gave a yellow oil which was distilled (a small amount of CaCO$_3$ was added) at reduced pressure (ca. 0.1 Torr) giving 6.7 g of the pure title substance as a colorless liquid (bp 65°–70° C.), together with 25° C.–65° C. (5.2 g) and 70°–80° C. (5.2 g) fractions. Separate distillation of these impure fractions separated less polar (TLC) lower and higher boiling contaminants, respectively, affording additional samples of product (total yield, 12.7 g, 54%): TLC Rf 0.15 ether-hexanes; $^1$H-NMR (300 mHz, CDCl$_3$) δ 0.97 (m, 2H), 1.07–1.93 (overlapping m, 15H), 4.12 (ddd, 1H, J=22, 10, ca 2 Hz), 4.52 (m, 1H).
[1]Normant, J. F.; Sauvetre, R. Tetrahedron Lett. 1981, 957–958.

B. methyl (E)-2-isobutyl-3,3-difluoro-6-cyclohexyl-4-hexenoate

A 500 mL three-necked flask was placed in an oil bath and equipped with thermometer, stopper and nitrogen line. In the nitrogen line was inserted a glass tee connected with a short length of tubing to a second, ice-cooled 25 mL flask which was positioned so as to prevent volatiles (methanol) distilling into the line from returning to the reaction mixture. The three-necked flask was charged with the product of Example 10A (84.0 g, 0.442 mol), trimethyl 4-methylorthovalerate[1] (156 g, 0.884 mol, 2.0 equiv) and pivalic acid (2.25 g, 22 mmol, 0.05 equiv) and the mixture was heated to 107° C. (internal) over 35 minutes. The reaction was monitored by 300 mHz $^1$H NMR for disappearance of starting material on aliquots diluted with CDCl$_3$. After 3 hours of heating no starting material was thereby observed and the mixture was cooled, diluted with ether (1.5 L), and the resulting solution was washed with aqueous 1N NaOH (3×60 mL), brine (100 mL) and dried over anhydrous K$_2$CO$_3$. The solution was concentrated by distillation (Vigreux column) first at atmospheric pressure then at 3 Torr to give (bp 39°–50° C., 112 g) impure unreacted orthoester. The distillation was continued at 0.25 Torr giving the product in two fractions (bp to 130° C., 26.1 g, impure and 130°–140° C., 82.5 g). Redistillation of the former gave an additional 10.9 g of product which was combined with the main fraction giving 93.4 g (70%) of product as a light yellow liquid: TLC Rf 0.6 (1:4 ether-hexanes); $^1$H NMR (300 mHz, CDCl$_3$) δ 0.85 and 0.87 (d, 3H ea, J=7 Hz), ca. 0.90 (m, 2H), 1.0–1.8 (overlapping m, ca. 14H), 1.96 (m, 2H), 2.96 (m, 1H), 3.65 (s, 3H), 5.52 (m, 1H), 6.00 (m, 1H).

C. (E)-2-isobutyl-3,3-difluoro-6-cyclohexyl-4-hexenal

A solution of the product of Example 10B (32.5 g, 0.107 mol) in hexane (100 mL) and toluene (50 mL) in a 2 L 4-necked flask equipped with addition funnel, overhead stirrer, thermometer and nitrogen inlet was cooled with stirring at −78° C. Diisobutylaluminum hydride (260 mL of 1.0M in hexane, 2.4 equiv) was added over 45 minutes (the reaction temperature was maintained below −68° C.), and the resulting mixture was stirred an additional 15 minutes at −78° C. Absolute methanol (44 mL) was added dropwise over 5 minutes and the mixture was stirred 10 minutes at −78° C. Ether (800 mL) was added, followed by aqueous Rochells salt solution (373 mL, 50 wt % Na-K tartrate tetrahydrate, the first several mL added slowly) and the mixture was warmed to 25° C. and stirred for 20 minutes. Following dissipation of the resulting emulsion the organic layer was separated and the aqueous layer extracted with ether (4×200 mL). The combined organic layers were washed with brine, dried over MgSO$_4$ and concentrated giving 30.3 (103%) g of product as a pale yellow liquid which was not purified. Aldehyde product thus prepared was essentially homogeneous by $^1$H NMR and TLC; this procedure, however, occasionally gave product containing 10–15% of a more polar substance spectrally characterized as the corresponding primary alcohol. The batches were likewise carried forward to the next step (oxidation) without purification or diminution of the subsequent yield. For product: TLC Rf 0.55 (1:20 ether-hexanes); $^1$H NMR (300 mHz, CDCl$_3$), 0.89 (d, 3H, J=7 Hz), 0.92 (d, 3H, J=7 Hz), 1.0–1.4 (overlapping m, ca. 6H), 1.6–2.0 (overlapping m, 8H), 2.02 (m, 2H), 2.83 (m, 1H), 5.48 (dt, J=15 Hz, 12 Hz), 6.07 (m, 1H), 9.67 (t, 1H, J=ca. 3 Hz).

D. (E)-2-isobutyl-3,3-difluoro-6-cyclohexyl-4-hexenoic acid

To a stirred 10° C. solution of crude product of Example 10C obtained in the preceding step (29.3, 0.103 mol, maximum) and ether (600 mL) in a 2L three-necked flask equipped with mechanical stirrer, dropping funnel, thermometer, and ice bath was added dropwise over 30 minutes a solution of chromic acid[2] (87 mL) so that the reaction temperature did not exceed 20° C. TLC indicated complete conversion of starting material to a more polar substance. The mixture was filtered through Celite which was washed well with ether. Additional ether (2 L) was added, a small lower layer decanted and the remaining organic layer was washed with 1N aqueous HCl (2×). The aqueous layer was separated, washed with ether (3×) and the organic layers were dried (Na$_2$SO$_4$) and concentrated. The dark brown residue was chromatographed on 1 kg silica packed in 1:20 ether-hexanes, loading and eluting with 6 L of this solvent followed by 6 L of 2:3 ether-hexanes giving 22.0 g (74% from the methyl ester of Example 10B) of product as a pale yellow oil. Analogous preparations of similar scale including those employing crude starting material containing up to 15% of the corresponding primary alcohol consistently afforded product in 70–80% yield. For product: TLC Rf 0.3 (3:5 ethyl acetate-hexanes); $^1$H NMR (300 mHz, CDCl$_3$) δ0.89 (d, 3H, J=7 Hz), 0.91 (d, 3H, J=7 Hz), 1.05-1.5 (m, ca. 6H), 1.5-1.9 (m, ca. 8H), 1.98 (m, 2H), 2.98 (m, 1H), 5.61 (m, 1H), 6.08 (m, 1H), 10.95 (br, 1H).

[2]Prepared as described in "Organic Syntheses"; Wiley, N.Y., 1973; Collect. Vol. V., p. 310.

E. (E)-2-isobutyl-3,3-difluoro-6-cyclohexyl-4-hexenamide

Oxalyl chloride (70 g, 0.55 mol, 9.3 equiv) was added over 3 minutes to a 15° C. solution of the product of Example 10D (17.1 g, 59.3 mmol) and dimethylformamide (50 μL, 0.6 mmol, 0.01 equiv) in dry toluene (80 mL) and the mixture was stirred at 25° C. for 24 hours. TLC (3:5 ethyl acetate-hexanes) of the organic layer of a concentrated, butylamine-treated aliquot partitioned between ether-1N HCl revealed a small amount (ca. 5%) of unreacted starting material. 100 μL dimethylformamide was added and the mixture was stirred an additional 2 hours at 25° C. (TLC as above indicated further conversion of residual starting material to the acid chloride. The mixture was concentrated to an oil (using a vacuum pump and −78° C. trap) which was dissolved in dry dichloromethane (200 mL) and cooled with stirring to 0° C. Anhydrous ammonia was introduced during 10 minutes into this solution. The reaction temperature rose rapidly (<1 minute) to 20° C. and persisted at 15° C. for most of this period. When the exotherm subsided introduction of ammonia was halted and the mixture was concentrated. The residue was dissolved in ethyl acetate, and the resulting solution was washed with $H_2O$ (3×), aqueous saturated $NaHCO_3$, dried ($MgSO_4$) and concentrated giving a pale yellow solid (17.4 g). Recrystallization from 100 mL hot hexanes afforded 13.1 g (77%) of product as a colorless solid, mp 72°-74.5° C. The mother liquors were concentrated and chromatographed on silica in 1:6 then 1:4 ethyl acetate-hexanes giving an additional 3.1 g (18%, total yield 95%) of product. For product:TLC Rf 0.35 (3:5 ethyl acetate-hexanes); $^1H$ NMR (CDCl$_3$, 300 mHz) δ0.93 and 0.95 (d, 3H ea, J=7 Hz), 1.16 (m, 4H), 1.34 (m, 2H), 1.67 (m, 8H), 2.03 (m, 2H), 2.84 (m, 1H), 5.58 (m, 1H), 5.65 and 5.73 (br, 1H), 6.1 (m, 1H).

F. (E)-2-isobutyl-3,3-difluoro-6-cyclohexyl-4-hexenimidic acid ethyl ester

A solution of freshly prepared[3] triethyloxonium tetrafluoborate (14 g, 74 mmol, 1.4 equiv) in dry chloromethane (40 mL) was added in one portion to a 25° C. solution of amide of Example 10E (15.2 g, 52.8 mmol) in dry dichloromethane (40 mL) and the resulting solution was stirred 24 hours at 25° C. The reaction mixture was diluted with ether (600 mL) and this solution was washed with saturated aqueous NaHCO$_3$ (3×100 mL), brine and dried over Na$_2$SO$_4$. 16.8 g of an orange oil obtained on solvent removal was chromatographed on 200 g silica eluting with 1:10 (2 L), followed by 1:1 ethyl acetate-hexanes. Concentration of the appropriate fractions gave the product as a light yellow liquid (15.8 g, 95%): TLC Rf 0.55 (3:5 ethyl acetate-hexanes); $^1H$ NMR (300 mHz, CDCl$_3$) δ0.86 and 0.89 (d, 3H ea, J=7 Hz), 1.0-1.7 (m, ca, 14H), 1.30 (t, 3H, J=7 Hz), 1.95 (m, 1H), 2.76 (m, 1H), 4.13 (dq, 2H, J=7 Hz, ca 2 Hz), 5.51 (m, 1H), 6.05 (m, 1H).

[3]"Organic Syntheses": Wiley, N.Y., 1973; Collect. Vol. V., p. 1080.

G. (±)-(3R*,5R*,6R*)-6-cyclohexylmethyl-4,4-difluoro-2-ethoxy-5-iodo-3,4,5,6-tetrahydropyridine Sodium bicarbonate (12.0 g, 143 mmol, 6 equiv) and iodine (12.3 g, 48.5 mmol, 2.0 equiv) were added sequentially at 25° C. to a 125 mL round-bottom flask containing a solution of iminoester product of Example 10F (7.56 g, 24.0 mmol) in acetonitrile (30 mL) and THF (30 mL). The vessel was partially immersed in the bath of an ultrasonic cleaner (Bransonic 221) and the mixture was sonicated for 24 hours (this operation resulted in a reaction temperature of 43° C.). The reaction mixture was diluted with ethyl acetate (400 mL) and the resulting solution was washed with aqueous 10% Na$_2$S$_2$O$_3$ (2×50 mL), aqueous saturated NaHCO$_3$ (50 mL), brine and dried over Na$_2$SO$_4$. The solution was concentrated and the residue chromatographed on silica (65 g) packed and loaded in 1:4:200 ether-triethylamine-hexanes. The fractions containing the product were combined (2 mL additional triethylamine was added) and concentrated giving an oil which crystallized as a waxy yellow low melting solid on drying (7.39 g, 70%). The structure and stereochemistry of the product were defined by single crystal X-ray analysis on a crystal grown by slow evaporation of this material from hexane. Further elution of the column with 1:9 ether-hexanes gave unreacted starting material (ca. 800 mg, 10%). For the product:TLC Rf 0.45 (5% ether-hexanes); 0.68 (1:3 ethyl acetate-hexanes); $^1H$ NMR (300 mHz, CDCl$_3$) ca. 10:1 mixture of two compounds, major δ0.91 (d, 6H, J=7 Hz), 1.21 (t, 3H, J=7 Hz), 1.05-1.45 (overlapping m, ca. 4H), 1.5-1.75 (overlapping m, ca. 8H), 1.84 (m, 2H), 2.85 (m, 1H), 3.75-3.90 (overlapping m, 2H), 4.02 (apparent dq, 2H, J=7 Hz, ca. 3 Hz), minor δ0.88 (d, J=7 Hz); $^{19}F$ (mHz, CDCl$_3$, 282 mHz, ppm downfield from CFCl$_3$) (ca. 10% of a second compound present) major δ79.6 (ddd, 1F, J=16, 26, 235 Hz), 83.5 (d, 1F, J=235 Hz), minor δ64.7 (ddd, 1F, J=235, 23, 29 Hz), 89.6 (dd, 1F, J=235, 10 Hz).

H. (±)-ethyl (2R*,4R*,5R*)-2-isobutyl-3,3-difluoro-4-iodo-5-amino-6-cyclohexylhexanoate Aqueous 1N HCl (50 mL, 2.2 equiv) was added at 0° C. to a solution of cyclic iminoether of Example 10G (10.1 g, 22.9 mmol) in THF. The mixture was stirred at 0° C. for 6.5 hours and allowed to stand unstirred at −20° C. for 15 hours. The solid was filtered and washed with 2:1 ether-THF (3×) and ether (4×) and dried giving the product as colorless crystals (4.76 g, 42%). The mother liquors were concentrated and dried giving crude product (6.63 g, 59%) as an amber solid. For product (crystalline lot): $^1H$ NMR (CDCl$_2$, 300 mHz) δ0.94 (m, ca. 1H), 0.90 (d, 3H, J=7 Hz), 0.92 (d, 3H, J=7 Hz), 1.27 (t, 3H, J=7 Hz), 1.05-1.42 (m, ca. 6H), 1.42-1.80 (m, ca. 8H), 1.91 (m, 2H), 3.38 (m, 2H), 4.21 (q, 2H, J=7 Hz), 5.16 (br d, 1H, J=22 Hz), 8.71 (br, 3H); $^{19}F$ NMR (CDCl$_3$, 282.2 mHz, ppm downfield from CFCl$_3$) δ72.2 (dd, 1F, J=247, 20 Hz), 84.3 (dd, 1F, J=247, 22 Hz).

I. (±)-ethyl (2R*,4R*,5R*)-2-isobutyl-3,3-difluoro-4-iodo-5-benzyloxycarbonylamino-6-cyclohexylhexanoate Benzyloxycarbonyl chloride (8.1 g, 5 equiv) was added in one portion to a well-stirred mixture of the product of Example 10H (crystalline lot, 4.76 g, 9.60 mmol) in THF (95 mL) and saturated aqueous NaHCO$_3$ (95 mL) at 0° C. After 15 minutes the mixture was partially concentrated and extracted with ether. The organic layers were washed with saturated aqueous NaHCO$_3$, brine, dried (MgSO$_4$) and concentrated giving a clear liquid which was chromatographed on silica (320 g) packed and loaded in 3% (v/v) ether-hexanes. Elution with 3% (2 L), 5% (2 L) and 10% (2 L) ether-hexanes gave the product (4.97 g, 87%) as a colorless oil. For product:TLC Rf 0.42 (1:4 ethyl acetate-hexanes); $^1H$ NMR (CDCl$_3$, 300 mHz) δ0.91 (d, 3H, J=7

Hz), 0.93 (d, 3H, J=7 Hz), 1.05–1.46 (overlapping m, ca 14H), 1.27 (t, 3H, J=7 Hz), 3.24 (m, 1H), 3.57 (m, 1H), 4.23 (q, 2H, J=7 Hz), 4.6–4.75 (overlapping m, 2H, J=7 Hz), 4.6–4.75 (overlapping m, 2H total), 5.04 (d, 1H, J=13 Hz), 5.12 (d, 1H, J=13 Hz), 7.33 (m, 5H); $^{19}$F NMR (CDCl$_3$, 282.2 mHz, ppm downfield from CFCl$_3$) δ76.7 (ddd, 1F, J=246, 16, ca. 16 Hz), 85.0 (ddd, J=246, 16, ca. 16 Hz); a minor amount (ca 10%) of another (possibly isomeric) substance was present $^{19}$F δ73.1 (d of m, 1F, ca. 250 Hz), 83.4 (d of m, 1F, ca 250 Hz).

J. (±)-ethyl (2R*,4S*,5R*)-2-isobutyl-3,3-difluoro-4-hydroxy-5-benzyloxycarbonylamino-6-6-cyclohexyl-hexanoate A solution of trifluoroperacetic acid (3.3 equiv) was prepared by the dropwise addition of trifluoroacetic anhydride (5.6 g, 26.8 mmol) to 70% hydrogen peroxide (750 mg, 22.1 mmol) in dichloromethane at 0° C. This solution was added over 3 minutes at 0° C. to a stirred mixture of iodoester product of Example 10I (3.97 g, 6.69 mmol) and Na$_2$HPO$_4$ (9.5 g, 10 equiv) in 35 mL dichloromethane. TLC (1:3 ethyl acetate-hexanes) showed 40% conversion of starting material to the more polar product. The reaction mixture was treated twice more at 0° C. with additional portions of trifluoroperacetic acid (3.3 equiv each, as above) resulting in complete consumption of starting material. Dichloromethane (100 mL) and water (50 mL) were added and the mixture was warmed to 25° C. The layers were separated and the aqueous layer was extracted with dichloromethane (5×30 mL). The combined organic layers were washed with saturated aqueous NaHCO$_3$, 10% aqueous Na$_2$S$_2$O$_3$, brine, dried (MgSO$_4$) and concentrated giving 3.2 g of yellow oil which was chromatographed on silica (300 g) packed and loaded in 7% (v/v) ether-hexanes. Elution with 10% (3 L), 25% (3 L) and 30% (3 L) ether-hexanes gave the product as a waxy solid (2.37 g, 73%). For product: TLC Rf 0.25 (1:3 ethyl acetate-hexanes); $^1$H NMR (CDCl$_3$, 300 mHz) δ0.88 (d, 3H, J=7 Hz), 0.91 (d, 3H, J=7 Hz), 1.05–1.4 (overlapping m, ca. 6H, 1.24 (t, 3H, J=7 Hz), 1.4–1.8 (overlapping m, ca. 8H), 1.82 (m, 2H), 3.18 (m, 1H), 3.72 (d of m, 1H, J=18 Hz), 3.94 (br, 1H), 4.08 (m, 1H), 4.15 (q, 2H, J=7 Hz), 5.0–5.2 (m, 3H), 7.29 (m, 5H); $^{19}$F NMR (CDCl$_3$, 282.2 mHz, ppm downfield from CFCl$_3$) δ63.5 (dd, 1F, J=260 Hz, 18 Hz), 67.1 (dd, 1F, J=260 Hz, 20–27 Hz).

K. (±)-ethyl (2R*,4S*,5R*)-2-isobutyl-3,3-difluoro-4-hydroxy-5-amino-6-cyclohexylhexanoate hydrochloride A mixture of the product of Example 10J (1.36 g, 2.81 mmol) and 10% Pd(OH)$_2$/C (Aldrich, 1 g) in 10:1 methanol-acetic acid (25 mL) was shaken under 50 p.s.i. hydrogen pressure for 1 hour, filtered through Celite, and concentrated giving a pale yellow oil which was coevaporated with anhydrous 4N HCl-dioxane (3×5 mL) and dried giving the product as a yellow foam (996 mg, 91%) which was used without purification in the next step. For product:TLC Rf 0.3 (18:2:1 v/v/v CHCl$_3$:EtOH:HOAc); $^1$H NMR (DMSO-d6, 300 mHz, partial) δ0.87 (d, 3H, J=7 Hz), 0.89 (d, 3H, J=7 Hz), 3.19 (m, 1H), 3.85 (d of m, 1H, J=20 Hz), 4.12 (m, 2H), 6.94 (br, 1H), 7.84 (br, 3H).

L. ethyl (2R*S*,4S*R*,5R*S*)-2-isobutyl-3,3-difluoro-4-hydroxy-5-N-(N-[morpholinocarbonyl-L-phenylalanyl]norleucyl)-amino-6-cyclohexyl-hexanoate Amine hydrochloride from Example 10K (78 mg, 0.202 mmol) was stirred in dimethoxyethane (1.0 mL) at 0° C. and treated sequentially with triethylamine (28 μL, 0.202 mmol, 1.0 equiv) and morpholino-1-carbonyl-L-Phe-L-Nle-OSu (99 mg, 0.202 mmol, 1.0 equiv). The mixture was allowed to warm to 20° C. over 18 hours, diluted with ethyl acetate, and the resulting solution washed with 1N HCl (2×), saturated aqueous NaHCO$_3$(2×), brine, dried MgSO$_4$) and concentrated giving a colorless foam which was chromatographed on silica (13 g) packed and loaded in 3:2 ethyl acetate-hexanes. The column was eluted with 3:2 ethyl acetate-hexanes (600 mL) giving the product, a colorless solid (80 mg, 55%), as a 1:1 mixture of isomers. For product TLC Rf 0.45 (ethyl acetate); $^1$H NMR (CDCl$_3$), 300 mHz, partial, 1H=area of a one-proton resonance in one of the isomers) δ0.88 (d, isobutyl CH$_3$ of both isomers), 0.86 (t, norleucyl CH$_3$), 1.23 and 1.25 (triplets, OCH$_2$CH$_3$ of each isomer), 2.93–3.08 (m, 2H), 3.08–3.32 (m, ca. 8H), 3.58 (m, 4H), 3.70 (d of m, 2H, J=ca. 20Hz), 4.04–4.24 (m, ca. 8H), 4.26–4.44 (m, ca. 8H), 4.62 (d, 1H, J=9 Hz), 4.89 (d, 1H, J=5 Hz), 4.93 (d, 1H, J=5 Hz), 5.07 (d, 1H, J=8 Hz), 6.44 (overlapping d, 2H), 6.80 (d, 1H, J=9 Hz), 6.98 (d, 1H, J=9 Hz), 7.10–7.35 (m, 10H); $^{19}$F NMR (CDCl$_3$, 282.2 mHz, ppm downfield from CFCl$_3$) δ61.3 (A of AB, ddd, 1F, J=253, 20, 10 Hz), 63.5 (A of AB, ddd, 1F, J=253, 16, 16 Hz), 64.8 (B of AB, dd, 1F, J=253, 17 Hz), 66.3 (B of AB, 1F, ddd, J=254, 11, 19 Hz).

M. ethyl (2S,5S)-2-isobutyl-3,3-difluoro-4-keto-5-N-(N-[morpholinocarbonyl-L-phenylalanyl]-L-norleucyl)-amino-6-cyclohexylhexanoate 1-(3-dimethylaminopropyl)-3-ethylcarbodiimide hydrochloride (DEC, 68 mg, 0.355 mmol, 6 equiv) and dichloroacetic acid (3 μL, 0.036 mmol, 0.6 equiv) were added sequentially to a solution of the product of Example 10 L (43 mg, 0.0595 mmol) in 120 μL dimethylsulfoxide and 120 μL toluene at 25° C. After 20 minutes another 3 μL dichloroacetic acid was added, followed 15 minutes later by 45 mg addition DEC. After another 30 minutes a solution of oxalic acid (32 mg) in methanol (300 μL) was added, and the mixture was stirred 5 minutes and diluted with ethyl acetate. This solution was washed with 1N HCl (2×5 mL), saturated aqueous NaHCO$_3$ (2×5 mL), dried (MgSO$_4$) and concentrated. The residue was chromatographed on silica (5 g) packed, loaded, and eluted with 2:3 ethyl acetate-hexanes giving product as a mixture with the 2R,5R isomer (colorless solid, 21 mg, 50%, TLC Rf 0.48, ethyl acetate). This mixture was separated by HPLC on a 0.96×25 cm Zorbax C-8 column eluted with 80:20 acetonitrile-water at 6.3 mL/min, 254 nM detection. Approximately 5 mg of the mixture was injected at once in 200 μL of mobile phase. Concentration of the two fractions gave the less retained isomer product (9 mg), and the more retained 2R,5R isomer (5 mg) which were distinguished on the basis of renin inhibitory potency (the 2S,5S product was the more active). For product:HPLC T$_{ret}$ 5.08 min (Zorbax C-8 4.6×250 mm, 1.5 mL/min 80/20 acetonitrile-water); $^1$H NMR (CDCl$_3$, 300 mHz δ0.87 (t, 3H, J=7 Hz), 0.90 (d, 3H, J=7 Hz), 0.92 (d, 3H, J=7 Hz), 1.25 (t, 3H, J=7 Hz), 1.45–1.95 (m, ca 12H), 3.08–3.15 (m, 2H), 3.28 (overlapping m, 5H), 3.61 (m, 4H), 4.16 (q, 2H, J=7 Hz), 4.34 (q, 1H), 4.55 (q, 1H), 5.08 (m, 1H), 6.54 (d, 1H), 6.68 (br, 1H), 7.16–7.37 (m, 5–7H); $^{19}$F NMR (CDCl$_3$, 282.2 mHz, ppm downfield from CFCl$_3$) δ67.1 (A of AB, dd, 1F, J=285, 16 Hz), 69.4 (B of AB, 1F, J=285, 16 Hz). For the 2R,5R product:RP-HPLC, as above, T$_{ret}$=5.46 min, $^1$H NMR (CDCl$_3$, 300 mHz) δ0.87 (t, 3H), 0.88 (d, 3H), 0.90 (d, 3H), 1.23–2.0 (m, ca. 14H), 3.01 (dd, 1H), 3.15–3.35 (m, 6H), 3.62 (m, 4H), 4.15 (q, 2H), 4.35–4.52 (m, 2H), 4.89 (br, 1H), 5.08 (m, 1H), 7.00 (d, 1H), 7.18–7.38 (m, 5–6H); $^{19}$F (CDCl$_3$, 282.2 mHz, ppm downfield from CFCl$_3$) δ66.5 (A of AB, dd, 1F, J=280, 16 Hz), 70.0 (B of AB, dd, 1F, J=280, 16 Hz).

PREPARATION 1

MorpholinocarbonylPheNle

A. Norleucine benzyl ester

According to the general procedure outlined in *J. Med. Chem.* 1986, Vol. 30, p. 3575, 15.0 g norleucine (Nle) was mixed with 200 ml benzyl alcohol and cooled to 0° C. Thionyl chloride (25 ml) was added dropwise over 15 minutes and the mixture was slowly heated to 90° C. with a fierce evolution of SO$_2$ occurring at about 50° C. After 2 hours at 90° C. the mixture was cooled to 0° C. and 25 ml more thionyl chloride was added. The mixture was then heated again at 90° C. for 2 hours, cooled, diluted with 1.6 liters ether and stored overnight at 0° C. The crystals which formed were filtered, washed with ether and dried to give 23.1 g of a damp solid which was recrystallized from 1:10 ethanol-ether, using 23 ml ethanol. The filtered and dried solid weighed 17.1 g, TLC Rf 0.25 in System C (the spotted plate was exposed to ammonia vapor and dried prior to elution).

B. (S)-2-Isocyanato-3-phenylpropionic acid benzyl ester

According to the procedure of Lombardino et al. (J. Med. Chem. 1964, 7, 97) 18.0 g L-phenylalanine benzyl ester hydrochloride in 150 ml toluene was stirred at reflux under an atmosphere of phosgene for 1.5H, cooled and concentrated to give a solid which was recrystallized from 120 ml hexane to give 16.1 g of colorless needles.

Anal. Calcd for C$_{17}$H$_{15}$NO$_3$: C, 72.59; H, 5.37; N, 4.98. Found: C, 72.32; H, 5.35; N, 4.92. MP 68°–72° C. [alpha]$_D^{23}$ −80.4° (c=1.02, CHCl$_3$). IR (CHCl$_3$) 2250, 1750 cm$^{-1}$.

C. MorpholinocarbonylPhe benzyl ester

The product of Preparation 1B was dissolved in 5 ml dichloromethane, treated at 25° C. with 930 ul morpholine and after 30 minutes the mixture was concentrated to a waxy solid which was recrystallized from hot 4:1 hexane-ethyl acetate, giving 1.92 g of the title substance, mp 87°–89° C. MS (chemical ionization, isobutane) 369 (MH+, base peak).

D. MorpholinocarbonylPhe

The product of Preparation 1C (1.85 g) was dissolved in 30 ml absolute methanol and 5 ml acetic acid and shaken with 0.5 g 10% Pd/C for 1 hour under a 53 psi hydrogen atmosphere. The suspension was filtered, concentrated, co-evaporated three times with added toluene and dried to give 1.43 g of a colorless foam.

E. MorpholinocarbonylPheNle benzyl ester

Following the procedure for preparation and purification of the product of Example 1, 2.12 g of the product of Preparation 1A and 2.63 g of the product of Preparation 1C gave 3.30 g of the title substance as a colorless foam, TLC Rf 0.5 in ethyl acetate on silica, HPLC ret. time 3.27 minutes 97% of total absorption to 25 minutes in 70/30 MeCN-pH 2.1 0.1M phosphate.

F. MorpholinocarbonylPheNle

The product of Preparation 1D (3.3 g) was shaken in 35 ml methanol and 7 ml acetic acid with 1.0 g 10% Pd/C for 45 minutes, filtered through Celite, concentrated, co-evaporated several times with toluene and ether and dried to give 2.9 g of a colorless solid, TLC Rf 0.2 in System C.

I claim:

1. A compound of the formula

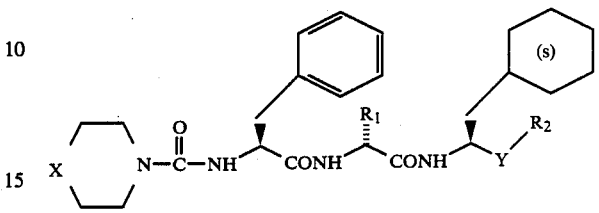

and a pharmaceutically acceptable salt thereof wherein X is O or NH; R$_1$ is alkyl having one to six carbon atoms, imidazol-4-ylmethyl or methylthiomethyl; Y is

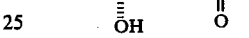

and R$_2$ is CF$_2$CONHCH$_3$, CF$_3$ or

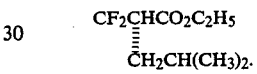

2. A compound of claim 1 wherein X is O and R$_1$ is alkyl having three to four carbon atoms.

3. The compound of claim 2 wherein R$_1$ is n-butyl, Y is CH┄OH and R$_2$ is CF$_2$CONHCH$_3$.

4. The compound of claim 2 wherein R$_1$ is n-butyl, Y is C=O and R$_2$ is CF$_2$CONHCH$_3$.

5. The compound of claim 2 wherein R$_1$ is n-butyl, Y is C=O and R$_2$ is CF$_3$.

6. The compound of claim 2 wherein R$_1$ is n-butyl, Y is CH┄OH and R$_2$ is CF$_3$.

7. The compound of claim 2 wherein R$_1$ is n-propyl, Y is CH┄OH and R$_2$ is CF$_2$CONHCH$_3$.

8. The compound of claim 2, wherein R$_1$ is n-butyl, Y is C=O and R$_2$ is

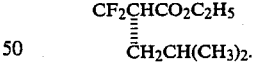

9. A compound of claim 1 wherein X is NH and R$_1$ is alkyl having from three to four carbon atoms.

10. The compound of claim 9 wherein R$_1$ is n-butyl, Y is CH┄OH and R$_2$ is CF$_2$CONHCH$_3$.

11. The compound of claim 9 wherein R$_1$ is n-butyl, Y is C=O and R$_2$ is CF$_2$CONHCH$_3$.

12. A method of treating hypertension in a mammal which comprises administering to said mammal an antihypertensive effective amount of a compound according to claim 1.

13. A pharmaceutical composition comprising an antihypertensive effective amount of a compound according to claim 1 and a pharmaceutically acceptable diluent or carrier.

* * * * *